US012715842B2

(12) United States Patent
Matsumoto et al.

(10) Patent No.: US 12,715,842 B2
(45) Date of Patent: Aug. 25, 2026

(54) D-LUCIFERIN, D-LUCIFERIN DERIVATIVE, PRECURSOR OF THESE COMPOUNDS AND METHOD FOR PRODUCING THESE COMPOUNDS

(71) Applicants: KANTO DENKA KOGYO CO., LTD., Tokyo (JP); KINKI UNIVERSITY, Osaka (JP)

(72) Inventors: Kouichi Matsumoto, Osaka (JP); Masafumi Kobayashi, Gunma (JP)

(73) Assignees: KANTO DENKA KOGYO CO., LTD., Tokyo (JP); KINKI UNIVERSITY, Osaka (JP)

( * ) Notice: Subject to any disclaimer, the term of this patent is extended or adjusted under 35 U.S.C. 154(b) by 504 days.

(21) Appl. No.: 18/551,230

(22) PCT Filed: Mar. 18, 2022

(86) PCT No.: PCT/JP2022/012857

§ 371 (c)(1),
(2) Date: Sep. 19, 2023

(87) PCT Pub. No.: WO2022/196819

PCT Pub. Date: Sep. 22, 2022

(65) Prior Publication Data

US 2024/0182410 A1 Jun. 6, 2024

(30) Foreign Application Priority Data

Mar. 19, 2021 (JP) ................................ 2021-046451

(51) Int. Cl.
*C07C 323/58* (2006.01)
*C07C 319/20* (2006.01)
*C07D 417/04* (2006.01)

(52) U.S. Cl.
CPC .......... *C07C 323/58* (2013.01); *C07C 319/20* (2013.01); *C07D 417/04* (2013.01)

(58) Field of Classification Search
CPC ...... C07C 23/58; C07C 319/20; C07D 417/04
See application file for complete search history.

(56) References Cited

U.S. PATENT DOCUMENTS

| | | | |
|---|---|---|---|
| 4,826,989 | A | 5/1989 | Batz et al. |
| 2007/0155806 | A1 | 7/2007 | Takakura et al. |
| 2011/0014599 | A1 | 1/2011 | Akhavan-Tafti et al. |
| 2014/0304842 | A1 | 10/2014 | Hitko |

FOREIGN PATENT DOCUMENTS

| | | | | | |
|---|---|---|---|---|---|
| CN | 1911917 | A | * | 2/2007 | |
| JP | S5616480 | A | | 2/1981 | |
| JP | 200791695 | A | | 4/2007 | |
| JP | 2010180191 | A | | 8/2010 | |
| JP | 2012533654 | A | | 12/2012 | |
| JP | 201968817 | A | | 5/2019 | |
| WO | WO 2019/021202 | | | 1/2019 | |
| WO | WO-2019021202 | A1 | * | 1/2019 | .......... C07D 277/68 |

OTHER PUBLICATIONS

Watthaisong, P. et al., A Chemo-enzymatic cascade for the smart detection of nitro- and halogenated phenols, Angewandte Chemie, Verlag Chemie Hoboken, USA, vol. 58, No. 38, pp. 13254-13258 (Year: 2019).*
J. Xavier et al. "The Structure and Synthesis of Firefly Luciferin", J. Am. Chem. Soc., 1961, 83(10), pp. 2402-2403.
S. Kanie, et al., "One-pot non-enzymatic formation of firefly luciferin in a neutral buffer from p-benzoquinone and cysteine" Scientific Reports, 2016, 6, pp. 1-8.
G. Li, et al.,"P(III)/P(V)-Catalyzed Methylamination of Arylboronic Acids and Esters: Reductive C—N Coupling with Nitromethane as a Methylamine Surrogate" J. Am. Chem. Soc., 2020, 142, pp. 16205-16210.
G. Pognon, et al. "Catechol-Modified Activated Carbon Prepared by the Diazonium Chemistry for Application as Active Electrode Material in Electrochemical Capacitor", ACS Appl. Mater. Interfaces, 2012, 4, pp. 3788-3796.
M. J. Bartels, et al.,"Synthesis of Stable Isotope-Labelled Analogs of the Cystejne and N-Acetylcysteine Conjugates of Tetrachloroethylene" J. Labelled Comp Radiopharm, 1990 28, 209-214.
D. C. McCutcheon, et al., "Expedient Synthesis of Electronically Modified Luciferins for Bioluminescence Imaging" J. Am. Chem. Soc., 2012, 134, 7604-7607.
International Search Report of PCT/JP2022/012857.
Extended Search Report in corresponding EP Application No. 22771561.2, dated Feb. 25, 2025, in 8 pgs.

(Continued)

*Primary Examiner* — Yate' K Cutliff
(74) *Attorney, Agent, or Firm* — Dority & Manning, PA

(57) ABSTRACT

To establish an unprecedented novel method for producing D-luciferin and a D-luciferin derivative without using expensive 2-cyano-6-hydroxybenzothiazole that is obtained by a multi-stage production process. In the method for producing D-luciferin and a D-luciferin derivative, the above object is achieved via a novel substituted diaminodithioether represented by the following formula (1):

(1)

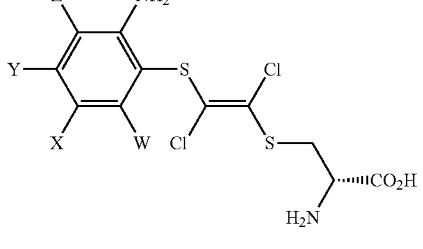

wherein X is H, $OCH_3$ or OH; and Y, Z and W are H or monovalent organic groups, which serves as a precursor.

15 Claims, No Drawings

(56) References Cited

OTHER PUBLICATIONS

Watthaisong, P., et al., A Chemo-Enzymatic Cascade for the Smart Detection of Nitro- and Halogenated Phenols, Angewandte Chemie, Verlag Chemie, Hoboken, USA, vol. 58, No. 38, Aug. 5, 2019, pp. 13254-13258, XP072097454, ISSN: 1433-7851, DOI: 10.1002/ANIE.201904923 (p. 13256; figure 2; compounds 2f, 2h).

* cited by examiner

D-LUCIFERIN, D-LUCIFERIN DERIVATIVE, PRECURSOR OF THESE COMPOUNDS AND METHOD FOR PRODUCING THESE COMPOUNDS

TECHNICAL FIELD

The present invention relates to a method for producing D-luciferin and a D-luciferin derivative, and a method for producing a precursor that is a raw material for producing D-luciferin and a D-luciferin derivative.

BACKGROUND ART

D-luciferin (firefly luciferin) is contained in fireflies and beetles and is a bioluminescent substance via the enzyme luciferase. Bioluminescence is more efficient than chemiluminescence and is characterized by almost no heat loss due to the reaction. Technology using bioluminescence is used in hygiene testing reagents to detect ATP from *Escherichia coli* (manufactured by Kikkoman Biochemifa Company), norovirus and Hepatitis C virus detection reagents (manufactured by Eiken Chemical), reporter gene assays (manufactured by TOYO B-Net), and the like. In the field of medical research, D-luciferin is beginning to gain attention as an important tool for bioimaging applications of such as cancer cells and stem cells, and recently, for in vivo luminescence imaging by increasing the emission wavelength (560 nm) of D-luciferin to the near-infrared region (650 to 900 nm), which is called the “biological window”.

There has been several proposals so far for the production of D-luciferin and D-luciferin derivatives modified with functional groups. Patent Literature 1 discloses a D-luciferin derivative modified with a functional group at the 7-position of the benzothiazole ring so that it emits light with luciferase and the emission wavelength is shifted towards the longer wavelength side. Patent Literature 2 discloses the synthesis of a D-luciferin derivative having a naphthothiazole ring, and this luciferin derivative is described as a long-wavelength, low-energy-emitting bioluminescent substance. Patent Literature 3 discloses a D-luciferin derivative in which the hydroxyl group at the 6-position of the benzothiazole ring is converted to an amino group in order to shift it to a longer wavelength. Patent Literature 4 discloses a D-luciferin derivative in which a substituent is introduced on the thiazole ring to stabilize D-luciferin in solution.

D-luciferin was first chemically synthesized by White et al. in 1961 (Non-Patent Literature 1). Later, improvements were made to the synthetic routes for D-luciferin and derivatives thereof, but all production methods used 2-cyano-6-hydroxybenzothiazole as a raw material (Patent Literatures 1 to 3).

For the synthesis of 2-cyano-6-hydroxybenzothiazole, various chemicals such as oxidizing agents, reducing agents, acids, bases, and organic metals are used, and it is synthesized through multiple steps. In addition, when used, it had to be purified to a high purity by silica gel column chromatography. As a method for synthesizing D-luciferin without using 2-cyano-6-hydroxybenzothiazole, there is a report in which D-luciferin was directly synthesized from benzoquinone and cysteine, but the yield was low and not suitable for industrialization (Non-Patent Literature 2).

CITATION LIST

Patent Literature

PTL 1: Japanese Patent Laid-Open No. 2010-180191 (7-Substituted luciferin derivative)

PTL 2: Japanese Patent Laid-Open No. 2019-68817 (Long-wavelength luciferin derivative naphthothiazole)

PTL 3: Japanese Patent Laid-Open No. 2007-91695 (6-Amino substituted luciferin derivative)

PTL 4: Japanese Translation of PCT International Application Publication No. 2012-533654 (5,5-Disubstituted luciferin derivative)

Non-Patent Literature

NPL 1: J. Am. Chem. Soc., 1961, 83 (10), 2402

NPL 2: Scientific Reports, 2016, 6, 24794

NPL 3: J. Am. Chem. Soc., 2020, 142, 16205

NPL 4: ACS Appl. Mater. Interfaces, 2012, 4, 3788

NPL 5: J. Labelled Comp Radiopharm, 1990, 28, 209

NPL 6: J. Am. Chem. Soc., 2012, 134, 7604

SUMMARY OF INVENTION

Technical Problem

Therefore, an object of the present invention is to establish an unprecedented novel method for producing D-luciferin and a D-luciferin derivative without using expensive 2-cyano-6-hydroxybenzothiazole that is obtained by a multi-stage production process.

Solution to Problem

The present invention includes the following aspects:

[1]

A substituted diaminodithioether represented by the following formula (1):

[Formula 1]

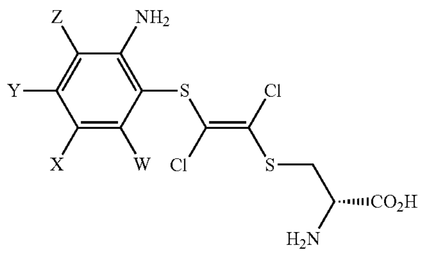

(1)

wherein X is H, $OCH_3$ or OH; and Y, Z and W are H or monovalent organic groups.

[2]

A method for producing a substituted diaminodithioether represented by the following formula (1):

[Formula 2]

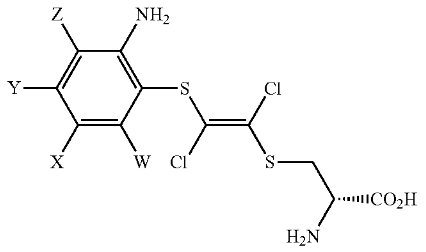

(1)

wherein X is H, $OCH_3$ or OH; and Y, Z and W are H or monovalent organic groups, the method including the step of:

(a) reacting a substituted D-cysteine represented by the following formula (2):

[Formula 3]

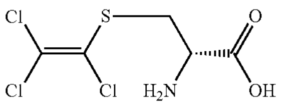

(2)

with an o-aminobenzenethiol derivative represented by the following formula (3):

[Formula 4]

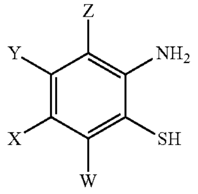

(3)

wherein X, Y, Z and W are as described above, in the presence of a base.

[3]

A method for producing D-luciferin and a D-luciferin derivative represented by the following formula (4):

[Formula 5]

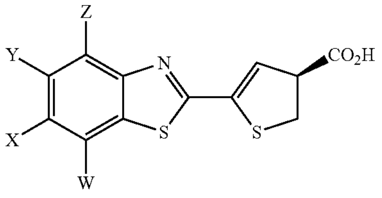

(4)

wherein X, Y, Z and W are as described above, the method including the step of:

(b) cyclizing the substituted diaminodithioether represented by formula (1) in the presence of a base.

[4]

The method for producing D-luciferin and a D-luciferin derivative represented by formula (4) according to [3], wherein the substituted diaminodithioether represented by formula (1) is obtained by the step (a) according to [2].

[5]

The method according to [2], wherein the substituted D-cysteine represented by formula (2) is obtained by reacting tetrachloroethylene with D-cysteine in the presence of a base.

[6]

A method for producing a substituted diaminodithioether represented by the following formula (1):

[Formula 6]

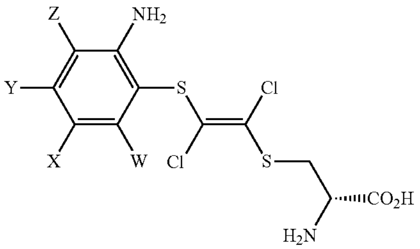

(1)

wherein X is H, $OCH_3$ or OH; and Y, Z and W are H or monovalent organic groups, the method including the step of:

(c) reacting an aminothioether derivative represented by the following formula (5):

[Formula 7]

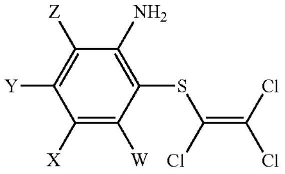

(5)

wherein X, Y, Z and W are as described above, with D-cysteine in the presence of a base.

[7]

The method for producing D-luciferin and a D-luciferin derivative represented by formula (4) according to [3], wherein the substituted diaminodithioether represented by formula (1) is obtained by the step (c) according to [6].

[8]

The method according to [6], wherein the aminothioether derivative represented by formula (5) is obtained by reacting an o-aminobenzenethiol derivative represented by the following formula (3):

[Formula 8]

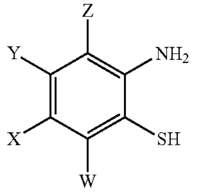

(3)

wherein X, Y, Z and W are as described above, with tetrachloroethylene in the presence of a base.

[9]

The method according to any of [2] to [8], wherein the base is selected from the group consisting of NaOH, DBN, and triethylamine.

Advantageous Effects of Invention

According to the present invention, it is possible to produce a precursor that serves as a raw material for producing D-luciferin and a D-luciferin derivative by an unprecedented novel production method that does not use expensive 2-cyano-6-hydroxybenzothiazole, and it is possible to easily produce D-luciferin and a D-luciferin derivative via this precursor.

DESCRIPTION OF EMBODIMENTS (Action)

The present invention relates to a method for producing D-luciferin and a D-luciferin derivative, but is characterized in that it goes through the novel substituted diaminodithioether represented by formula (1) which serves as a precursor. It was found for the first time by the present inventor that the substituted diaminodithioether of formula (1) can be produced by a novel two-stage sulfidation reaction using an aminobenzenethiol derivative represented by the following formula (3):

[Formula 10]

(3)

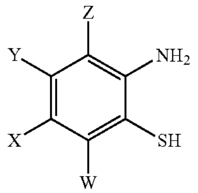

wherein X, Y, Z and W are as described above,
which is obtained by hydrolyzing a benzothiazole derivative represented by the following formula (6):

[Formula 9]

(6)

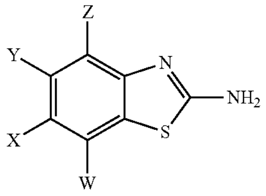

wherein X, Y, Z and W are as described above,
which is relatively easy to obtain, D-cysteine and tetrachloroethylene. For the substituted diaminodithioether of formula (1), the following two synthetic routes have been found, depending on the order in which the sulfidation reaction is carried out. The novel substituted diaminodithioether of formula (1) can be easily cyclized in the presence of a base and converted to D-luciferin and D-luciferin derivatives.

The following describes in detail the production method of the present invention.

(Precursor Compound of Formula (1))

In formula (1), Y, Z, and W may be H, or monovalent organic groups that do not affect the reaction, with examples thereof including alkyl groups, N,N-disubstituted amino groups, alkoxy groups, aryl groups, and aryloxy groups. Examples of alkyl groups include alkyl groups having 1 to 4 carbon atoms, particularly a methyl group, an ethyl group, an n-propyl group, an isopropyl group, an n-butyl group, an isobutyl group, and a t-butyl group. Examples of alkoxy groups include alkoxy groups having 1 to 4 carbon atoms, particularly a methoxy group, an ethoxy group, an n-propyloxy group, an isopropyloxy group, an n-butyloxy group, an isobutyloxy group, and a t-butyloxy group. Examples of aryl groups include a phenyl group, a naphthyl group, an anthranyl group, a naphthacenyl group, and a pentacenyl group. Examples of aryloxy groups include a phenyloxy group, a naphthyloxy group, an anthranyloxy group, a naphthacenyloxy group, and a pentacenyloxy group. Examples of N,N-disubstituted amino groups include those with two substituents such as the alkyl groups having 1 to 4 carbon atoms, aryl groups, and the like described above bound to the nitrogen of an amino group, and these two substituents may be the same or different. More specific examples include a dimethylamino group, a diethylamino group, an ethylmethylamino group, and a diisopropylamino group.

In the precursor of formula (1) that gives D-luciferin after the cyclization reaction, X is OH and Y, Z and W are H.

(First Synthetic Route)

The first synthetic route is a route including the step of:

(a) reacting a substituted D-cysteine represented by the following formula (2):

[Formula 11]

(2)

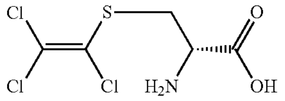

with an o-aminobenzenethiol derivative represented by the following formula (3):

[Formula 12]

(3)

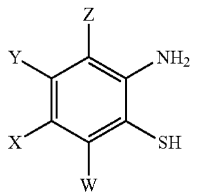

wherein X, Y, Z and W are as described above,
in the presence of a base. The conditions for the above sulfidation reaction (thioether formation reaction) are as follows.

Specific examples of the base: alkali metal hydroxides (e.g., sodium hydroxide and potassium hydroxide), quaternary ammonium salts (e.g., tetrabutylammonium fluoride), tertiary amines (e.g., triethylamine), strong organic bases (e.g., DBN (1,5-diazabicyclo[4.3.0]non-5-ene) and MTBD (7-methyl-1,5,7-triazabicyclo[4.4.0]dec-5-ene)), preferably, sodium hydroxide, triethylamine, DBN, and more preferably triethylamine.

Specific examples of the solvent: polar solvents, preferably dimethylformamide (DMF), N-methylpyrrolidone (NMP), dimethyl sulfoxide (DMSO), alcohols such as methanol, ethanol, propanol, and butanol, and more preferably DMF.

Reaction temperature: −100 to 200° C., preferably 0 to 100° C., and more preferably 25 to 60° C.

Other conditions: The mole equivalent number of the o-aminobenzenethiol derivative is 0.01 to 100 molar equivalents, preferably 0.1 to 10 molar equivalents, and more preferably 0.5 to 2 molar equivalents with respect to the substituted D-cysteine.

The mole equivalent number of the base is 0.01 to 100 molar equivalents, preferably 0.1 to 10 molar equivalents, and more preferably 1 to 3 molar equivalents with respect to the substituted D-cysteine.

The o-aminobenzenethiol derivative may be used in its free state or as a hydrogen chloride adduct.

The substituted D-cysteine represented by formula (2) is obtained, for example, by reacting tetrachloroethylene with D-cysteine in the presence of a base. The conditions for the above sulfidation reaction (thioether formation reaction) are as follows.

Specific examples of the base: alkali metal hydroxides (e.g., sodium hydroxide and potassium hydroxide), quaternary ammonium salts (e.g., tetrabutylammonium fluoride), tertiary amines (e.g., triethylamine), strong organic bases (e.g., DBN (1,5-diazabicyclo[4.3.0]non-5-ene) and MTBD (7-methyl-1,5,7-triazabicyclo[4.4.0]dec-5-ene)), preferably, sodium hydroxide, triethylamine, DBN, and more preferably DBN.

Specific examples of the solvent: polar solvents, preferably DMF, NMP, DMSO, alcohols such as methanol, ethanol, propanol, and butanol, and more preferably DMSO.

Reaction temperature: −100 to 200° C., preferably 0 to 100° C., and more preferably 25 to 60° C.

Other conditions: The mole equivalent number of tetrachloroethylene is 0.01 to 100 molar equivalents, preferably 0.1 to 10 molar equivalents, and more preferably 1 to 7 molar equivalents with respect to D-cysteine.

The mole equivalent number of the base is 0.01 to 100 molar equivalents, preferably 0.1 to 10 molar equivalents, and more preferably 1 to 3 molar equivalents with respect to D-cysteine.

D-cysteine may be used in its free state or as a hydrate, hydrogen chloride adduct.

(Second Synthetic Route)

The second synthetic route is a route including the step of:

(c) reacting a substituted o-aminothioether represented by the following formula (5):

[Formula 13]

(5)

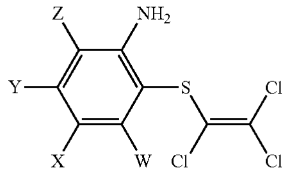

wherein X, Y, Z and W are as described above, with D-cysteine in the presence of a base. The conditions for the above sulfidation reaction (thioether formation reaction) are as follows.

Specific examples of the base: alkali metal hydroxides (e.g., sodium hydroxide and potassium hydroxide), quaternary ammonium salts (e.g., tetrabutylammonium fluoride), tertiary amines (e.g., triethylamine), strong organic bases (e.g., DBN (1,5-diazabicyclo[4.3.0]non-5-ene) and MTBD (7-methyl-1,5,7-triazabicyclo[4.4.0]dec-5-ene)), preferably, sodium hydroxide, triethylamine, DBN, and more preferably DBN.

Specific examples of the solvent: polar solvents, preferably DMF, NMP, DMSO, alcohols such as methanol, ethanol, propanol, and butanol, and more preferably DMSO.

Reaction temperature: −100 to 200° C., preferably 0 to 100° C., and more preferably 25 to 60° C.

Other conditions: The mole equivalent number of the substituted o-aminothioether is 0.01 to 100 molar equivalents, preferably 0.1 to 10 molar equivalents, and more preferably 1 to 10 molar equivalents with respect to D-cysteine.

The mole equivalent number of the base is 0.01 to 100 molar equivalents, preferably 0.1 to 10 molar equivalents, and more preferably 0.5 to 3 molar equivalents with respect to D-cysteine.

D-cysteine may be used in its free state or as a hydrate, hydrogen chloride adduct.

The substituted aminothioether represented by formula (5) is obtained, for example, by reacting an o-aminobenzenethiol derivative represented by the following formula (3):

[Formula 14]

(3)

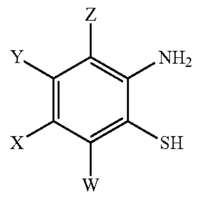

wherein X, Y, Z and W are as described above, with tetrachloroethylene in the presence of a base. The conditions for the above sulfidation reaction (thioether formation reaction) are as follows.

Specific examples of the base: alkali metal hydroxides (e.g., sodium hydroxide and potassium hydroxide), quaternary ammonium salts (e.g., tetrabutylammonium fluoride), tertiary amines (e.g., triethylamine), strong organic bases (e.g., DBN (1,5-diazabicyclo[4.3.0]non-5-ene) and MTBD (7-methyl-1,5,7-triazabicyclo[4.4.0]dec-5-ene)), preferably, sodium hydroxide, triethylamine, DBN, and more preferably sodium hydroxide.

Specific examples of the solvent: polar solvents, preferably DMF, NMP, DMSO, alcohols such as methanol, ethanol, propanol, and butanol, and more preferably DMSO.

Reaction temperature: −100 to 200° C., preferably 0 to 100° C., and more preferably 25 to 60° C.

Other conditions: The mole equivalent number of tetrachloroethylene is 0.01 to 100 molar equivalents, preferably 0.1 to 10 molar equivalents, and more preferably 0.5 to 5 molar equivalents with respect to the o-aminobenzenethiol derivative.

The mole equivalent number of the base is 0.01 to 100 molar equivalents, preferably 0.1 to 10 molar equivalents, and more preferably 1 to 3 molar equivalents with respect to the o-aminobenzenethiol derivative.

The o-aminobenzenethiol derivative may be used in its free state or as a hydrogen chloride adduct.

The o-aminobenzenethiol derivative represented by formula (3), which is an important raw material to perform the method of the present invention, is obtained, for example, by hydrolyzing a benzothiazole derivative represented by the following formula (6):

[Formula 15]

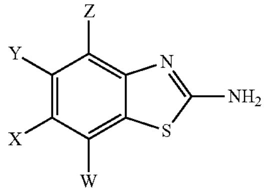

(6)

wherein X, Y, Z and W are as described above, which is relatively easy to obtain. This hydrolysis reaction can be easily performed by heating under alkaline conditions, for example, by heating and refluxing in a potassium hydroxide solution.

(Cyclization Reaction of Precursor)

The final target compounds of the present invention, D-luciferin and a D-luciferin derivative represented by the following formula (4):

[Formula 16]

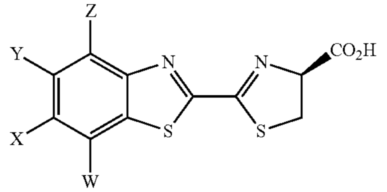

(4)

wherein X, Y, Z and W are as described above, can be obtained by a step of cyclizing the substituted diaminodithioether represented by formula (1) obtained by the first or second route in the presence of a base. Alternatively, they can be obtained by a step of cyclizing the substituted diaminodithioether represented by formula (1) by reacting the substituted D-cysteine represented by formula (2) with the o-aminobenzenethiol derivative represented by formula (3) in the presence of a base and continuing the reaction under the same reaction conditions without isolating the substituted diaminodithioether, or by a step of cyclizing the substituted diaminodithioether represented by formula (1) by reacting the aminothioether derivative represented by formula (5) with D-cysteine in the presence of a base and continuing the reaction under the same reaction conditions without isolating the substituted diaminodithioether. The conditions for the above cyclization reactions are as follows.

Specific examples of the base: alkali metal hydroxides (e.g., sodium hydroxide and potassium hydroxide), quaternary ammonium salts (e.g., tetrabutylammonium fluoride), tertiary amines (e.g., triethylamine), strong organic bases (e.g., DBN (1,5-diazabicyclo[4.3.0]non-5-ene) and MTBD (7-methyl-1,5,7-triazabicyclo[4.4.0]dec-5-ene)), preferably, sodium hydroxide, triethylamine, DBN, and more preferably triethylamine.

Specific examples of the solvent: polar solvents, preferably DMF, NMP, DMSO, methanol, ethanol, propanol, and butanol, and more preferably DMF.

Reaction temperature: −100 to 200° C., preferably 0 to 100° C., and more preferably 25 to 60° C.

Other conditions: The mole equivalent number of the base is 0.01 to 100 molar equivalents, preferably 0.1 to 10 molar equivalents, and more preferably 1 to 3 molar equivalents with respect to the substituted diaminodithioether.

The cyclization reactions can be performed via the reactions of the first or second route, each in the presence of a base, and these reactions can be performed continuously to produce the final target products. The reaction conditions for continuously performing such a series of reactions are as follows.

Specific examples of the base: alkali metal hydroxides (e.g., sodium hydroxide and potassium hydroxide), quaternary ammonium salts (e.g., tetrabutylammonium fluoride), tertiary amines (e.g., triethylamine), strong organic bases (e.g., DBN (1,5-diazabicyclo[4.3.0]non-5-ene) and MTBD (7-methyl-1,5,7-triazabicyclo[4.4.0]dec-5-ene)), preferably, sodium hydroxide, triethylamine, DBN, and more preferably triethylamine.

Specific examples of the solvent: polar solvents, preferably DMF, NMP, DMSO, methanol, ethanol, propanol, and butanol, and more preferably DMF.

Reaction temperature: −100 to 200° C., preferably 0 to 100° C., and more preferably 25 to 60° C.

Other conditions: The mole equivalent number of the base is 0.01 to 100 molar equivalents, preferably 0.1 to 10 molar equivalents, and more preferably 2 to 6 molar equivalents with respect to the total mole equivalent number of the o-aminobenzene derivative and D-cysteine.

Since common bases and solvents can be used in this series of reactions, the reaction reagents can be sequentially charged using a single reactor, which allows to induce the intermediate substituted diaminodithioether into the final target product by a series of sulfidation and cyclization reactions without isolating it. That is, tetrachloroethylene is sequentially reacted with D-cysteine and an o-aminobenzene derivative to be induced into a substituted diaminodithioether, which is cyclized as it is to obtain D-luciferin and a D-luciferin derivative. Thus, according to the present invention, the process of producing D-luciferin and a D-luciferin derivative via the novel precursor of formula (1) can be made relatively simple.

(Reaction Apparatus)

A reaction apparatus used for general organic synthesis can be used.

EXAMPLES

Hereinafter, the present invention is described specifically based on Examples, but the scope of the present invention is not limited to these Examples. Of the reagents used in the Examples shown below, the tetrachloroethylene used was the one manufactured by Kanto Denka Kogyo Co., Ltd. 2-Amino-5-methoxybenzenethiol was produced by the method shown in Non-Patent Literature 3 (J. Am. Chem. Soc., 2020, 142, 16205). 2-Amino-5-hydroxybenzenethiol and substituted 2-amino-5-hydroxybenzenethiol were produced from the corresponding 2-amino-5-methoxybenzenethiol and substituted 2-amino-5-methoxybenzenethiol by referring to the demethylation reaction of the methoxy group shown in Non-Patent Literature 4 (ACS Appl. Mater. Interfaces, 2012, 4, 3788). Substituted D-cysteine was produced by the method shown in Non-Patent Literature 5 (J. Labelled Comp Radiopharm, 1990, 28, 209). The other reagents and solvents were obtained from chemical manufacturers such as Aldrich, Tokyo Chemical, FUJIFILM Wako Pure Chemical, SASAKI CHEMICAL, Nacalai Tesque, and Kanto Chemical. For the recycling HPLC, LC-9201, LC-9110 NEXT or LC-9210 NEXT equipped with JAIGEL-1H and JAIGEL-2H from Japan Analytical Industry was used. HRMS (Thermo Fisher Scientific EXACTIVE Plus) and NMR (MERCURY 300 manufactured by Varian and JNM-ECS 400 manufactured by JEOL) were used for analysis. HPLC analysis was performed by an apparatus consisting of a pump LC20AD, a detector SPD-M40A (detection at 254 nm), a column oven CTO-20A, and an autosampler SIL-20ACHT manufactured by Shimadzu Corporation. In addition, the column used was L-Column2ODS 3 μm (4.6 mmϕ×250 mm), and as the eluent, ultrapure water (Wako) containing 0.01% acetic acid and acetonitrile (Wako) containing 0.01% acetic acid were used to perform the analysis.

(Example 1) Production of 2-Amino-5-methoxybenzenethiol (NPL 3: J. Am. Chem. Soc., 2020, 142, 16205)

[Formula 17]

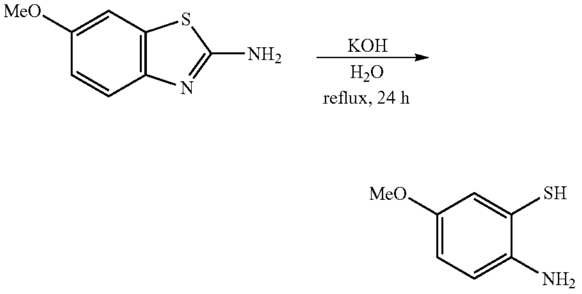

wherein Me represents a methyl group.

To a glass flask was added 2.96 g, 16.4 mmol of 2-amino-6-methoxybenzothiazole and 12 mL of a 23% KOH aqueous solution, and the mixture was allowed to react under reflux for 24 hours. Heating was stopped, and the mixture was brought back to room temperature, and adjusted to pH 4 to 5 with 10 mL of 6M HCl aqueous solution. Filtration was performed with a Kiriyama funnel and the solid was washed with distilled water. The solid was dried under reduced pressure and purified twice by column chromatography to give 1.36 g of 2-amino-5-methoxybenzenethiol with a 53% yield with respect to 2-amino-6-methoxybenzothiazole.

$^1$H NMR (300 MHz, $CDCl_3$) δ 3.61 (s, 3H), 3.86-4.30 (br, s, 2H), 6.692 (d, J=3.0 Hz, 1H), 6.693 (d, J=8.7 Hz, 1H), 6.81 (dd, J=8.7 Hz, 3.0 Hz, 1H). $^{13}$C NMR (75 MHZ, $CDCl_3$) δ 55.7, 116.6, 119.2, 119.3, 120.0, 142.6, 151.8.

HRMS (ESI, positive) calcd for $C_7H_{10}NOS$ $[M+H]^+$ 156.0478; found 156.0470.

(Example 2) Production of 2-Amino-5-hydroxybenzenethiol (NPL 4: ACS Appl. Mater. Interfaces, 2012, 4, 3788)

[Formula 18]

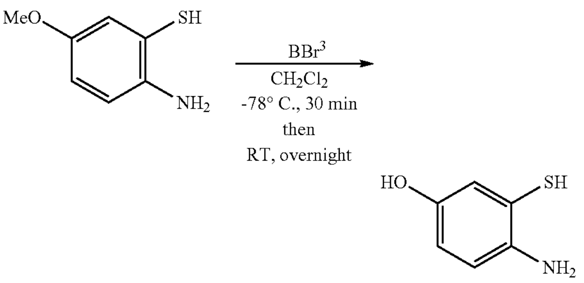

wherein Me represents a methyl group.

315.8 mg, 2.0 mmol of 2-amino-5-methoxybenzenethiol was placed in a glass flask and dissolved in 7 mL of $CH_2Cl_2$. Then, the mixture was immersed in an acetone/dry ice bath at −78° C., and $BBr_3$ (7 mL of 1M $CH_2Cl_2$ solution) was added dropwise. After the dropwise addition, stirring was continued for 30 minutes, then the temperature was raised to room temperature and the mixture was allowed to react overnight. 10 mL of methanol was added dropwise to the reaction solution to stop the reaction, and then $CH_2Cl_2$ was evaporated to concentrate the reaction solution. After removing the solid precipitated with chloroform and methanol, the liquid was concentrated to give quantitative 2-amino-5-hydroxybenzenethiol.

$^1$H NMR (400 MHZ, $CD_3OD$) δ 6.74 (dd, J=8.4, 2.8 Hz, 1H), 7.01 (d, J=2.8 Hz, 1H), 7.22 (d, J=8.4 Hz, 1H)

HRMS (ESI, positive) calcd for $C_6H_8NOS$ $[M+H]^+$ 142.0321; found 142.0322.

(Examples 3) Production of Substituted D-cysteine (NPL 5: J. Labelled Comp Radiopharm, 1990, 28, 209)

[Formula 19]

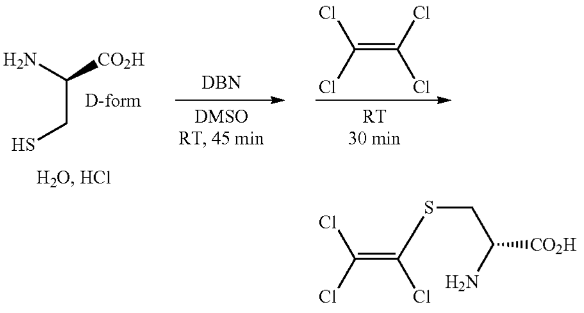

Substituted D-cysteine

To a glass flask was added 0.86 g, 4.9 mmol of D-cysteine hydrochloride monohydrate, 10 mL of DMSO, and 1.60 g, 12.9 mmol of DBN, and the mixture was stirred at room temperature for 45 minutes. Then, 5.38 g, 32.4 mmol of tetrachloroethylene was added and the mixture was further stirred at room temperature for 30 minutes. 40 mL of distilled water was added to stop the reaction, and then the mixture was adjusted to pH 4 with acetic acid. The mixture was cooled in a thermostatic bath at −10.9° C., and stirred for 1 hour. Substituted D-cysteine was obtained by filtration with an 83% yield with respect to D-cysteine hydrochloride monohydrate.

$^1$H NMR (400 MHZ, $D_2O$/NaOH) δ 2.98 (dd, J=13.8, 6.6 Hz, 1H), 3.10 (dd, J=13.8, 5.0 Hz, 1H), 3.26 (dd, J=7.0, 5.0 Hz, 1H).

HRMS (ESI, negative) calcd for $C_5H_5Cl_3NO_2S$ $[M-H]^-$ 247.9112; found 247.9106.

(Example 4) Production of Substituted 2-Aminobenzenethiol 1A

[Formula 20]

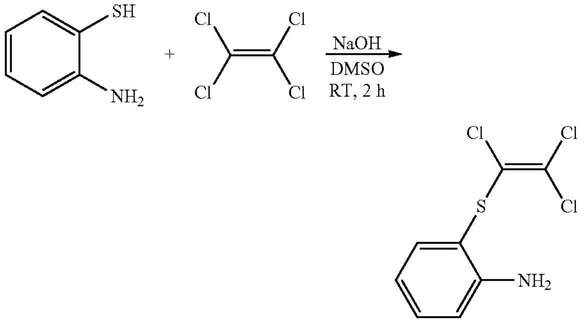

1A

To a glass flask was added 4 ml. of DMSO, 1.678 g, 10.1 mmol of tetrachloroethylene, 0.1187 g, 3.0 mmol of NaOH, and 0.249 g, 1.9 mmol of 2-aminobenzenethiol, and the mixture was allowed to react at room temperature for 2 hours. 5 mL of distilled water was added to stop the reaction, followed by extraction with diethyl ether ($Et_2O$) (15 mL×3), and the organic layer was washed with saturated brine (15 mL×3). The organic layer was dried over magnesium sulfate, and then filtered. The filtrate was concentrated, then purified by column chromatography to give 215.8 mg of substituted 2-aminobenzenethiol (Novel Compound 1A) with a 45% yield with respect to 2-aminobenzenethiol.

$^1$H NMR (300 MHz, $CDCl_3$) δ 4.31 (br, s, 2H), 6.70-6.80 (m, 2H), 7.20-7.28 (m, 1H), 7.42 (dd, J=7.8, 1.2 Hz, 1H).

HRMS (ESI, positive) calcd for $C_8H_7NCl_3S$ $[M+H]^+$ 253.9359; found 253.9355.

(Example 5) Production of Substituted 2-Amino-5-methoxybenzenethiol 1B

[Formula 21]

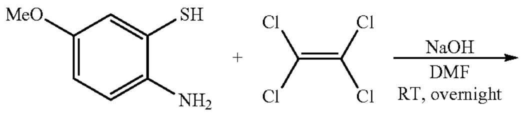

-continued

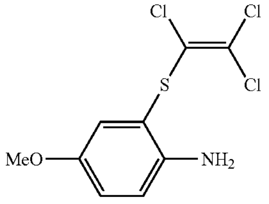

1B wherein Me represents a methyl group.

To a glass flask was added 20 mL of DMF, 4.68 g, 28.2 mmol of tetrachloroethylene, 0.57 g, 14.3 mmol of NaOH, 1.11 g, 7.2 mmol of 2-amino-5-methoxybenzenethiol, and the mixture was allowed to react overnight at room temperature. 20 mL of distilled water was added to stop the reaction, followed by extraction with ethyl acetate (AcOEt) (40 mL×3), and the organic layer was washed with water (40 mL×2) and saturated brine (40 mL×1). The organic layer was dried over sodium sulfate. After filtration, the organic layer was concentrated, and purified by column chromatography to give 0.33 g of substituted 2-amino-5-methoxybenzenethiol (Novel Compound 1B) with a 16% yield with respect to 2-amino-5-methoxybenzenethiol.

$^1$H NMR (300 MHZ, $CDCl_3$) δ 3.76 (s, 3H), 4.02 (br, s, 2H), 6.73 (d, J=8.7 Hz, 1H), 6.88 (dd, J=8.7, 3.0 Hz, 1H), 6.97 (d, J=3.0 Hz, 1H).

$^{13}$C NMR (75 MHz, $CDCl_3$) δ 55.9, 112.9, 116.5, 116.7, 119.3, 121.0, 127.1, 143.2, 152.1.

HRMS (ESI, positive) calcd for $C_9H_9ONCl_3S$ $[M+H]^+$ 283.9465; found 283.9460.

(Example 6) Production of Substituted 2-Amino-5-hydroxybenzenethiol 1C (NPL 4: ACS Appl. Mater. Interfaces, 2012, 4, 3788)

[Formula 22]

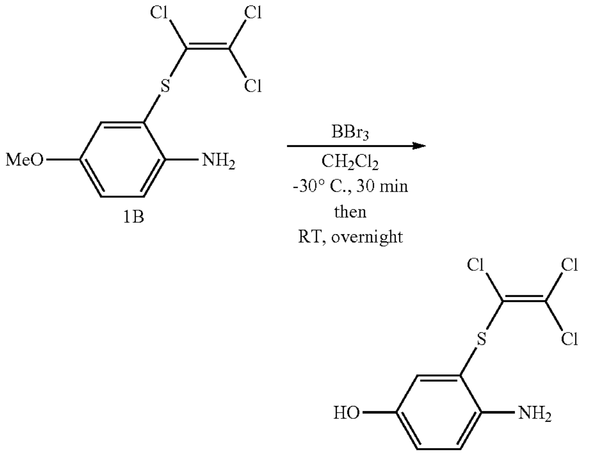

1C wherein Me represents a methyl group.

In a glass flask, 263.3 mg, 0.93 mmol of substituted 2-amino-5-methoxybenzenethiol 1B was dissolved in 5 mL of $CH_2Cl_2$ and the mixture was stirred in a thermostatic bath at −30° C. 3 mmol, 3 mL of 1M $BBr_3/CH_2Cl_2$ solution was added dropwise. After the dropwise addition, the mixture was stirred for 30 minutes at −30° C., then the temperature was raised to room temperature and the stirring was continued overnight. 10 mL of methanol was added to stop the reaction, followed by concentration, and reprecipitation with methanol and $Et_2O$. The solid was collected and vacuum dried to give 222.2 mg of substituted 2-amino-5-hydroxybenzenethiol (Novel Compound 1C), with an 88% yield with respect to substituted 2-amino-5-methoxybenzenethiol 1B.

$^1H$ NMR (400 MHZ, $CD_3OD$) δ 6.99 (dd, J=8.8, 2.8 Hz, 1H), 7.05 (d, J=2.8 Hz, 1H), 7.35 (d, J=8.8 Hz, 1H).

HRMS (ESI, negative) calcd for $C_3H_5Cl_3NOS$ $[M-H]^-$ 267.9163; found 267.9160.

(Example 7) Production of Substituted Diaminodithioether 2B

[Formula 23]

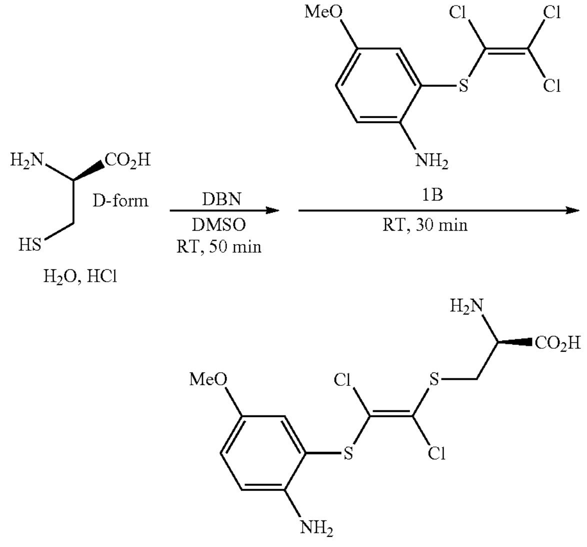

2B wherein Me represents a methyl group.

To a glass flask was added 88.1 mg, 0.5 mmol of D-cysteine hydrochloride monohydrate, 1 mL of DMSO, and 157.3 mg, 1.3 mmol of DBN, and the mixture was stirred at room temperature for 50 minutes. Then, 141.8 mg, 0.5 mmol of substituted 2-amino-5-methoxybenzenethiol 1B was added and the mixture was stirred at room temperature for 30 minutes. 4 mL of distilled water was added to stop the reaction and the mixture was adjusted to pH 4 with acetic acid. The reactor was immersed in an ice bath (−8° C.) with salt, and the mixture was stirred for 2 hours, and filtered to give 143.3 mg of substituted diaminodithioether (Novel Compound 2B) with a 78% yield with respect to substituted 2-amino-5-methoxybenzenethiol 1B.

$^1H$ NMR (400 MHZ, $D_2O$/NaOH) δ 2.88 (dd, J=13.8, 7.4 Hz, 1H), 3.14 (dd, J=13.8, 4.6 Hz, 1H), 3.21 (dd, J=7.2, 4.4 Hz, 1H), 3.54 (s, 3H), 6.69 (d, J=9.2 Hz, 1H), 6.77 (dd, J=8.8, 2.8 Hz, 1H), 6.85 (d, J=2.8 Hz, 1H).

HRMS (ESI, negative) calcd for $C_{12}H_{13}N_2O_3Cl_2S2$ $[M-H]^-$ 366.9750; found 366.9750.

(Example 8) Production of Substituted Diaminodithioether 2C

[Formula 24]

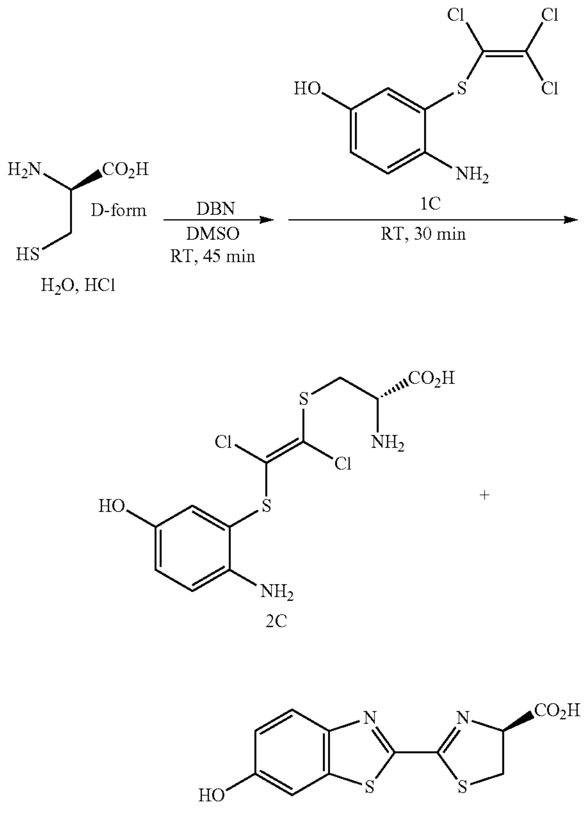

3C

To a glass flask was added 70.9 mg, 0.4 mmol of D-cysteine hydrochloride monohydrate, which was dissolved in 1 mL of DMSO. To this was added 124.9 mg, 1.0 mmol of DBN, and the mixture was stirred for 45 minutes. To this was added 108.8 mg. 0.40 mmol of substituted 2-amino-5-hydroxybenzenethiol (Novel Compound 1C). After stirring the mixture for 30 minutes, 4 mL of water was added to stop the reaction. The mixture was adjusted to pH 4 with acetic acid and cooled in an ice bath (−9° C.) with salt to precipitate a solid, which was filtered and vacuum dried to give 69.2 mg of solid substituted diaminodithioether (Novel Compound 2C) with a 50% yield with respect to substituted 2-amino-5-hydroxybenzenethiol 1C.

$^1H$ NMR (400 MHZ, $D_2O$/NaOH) δ 2.91 (dd, J=13.8, 7.4 Hz, 1H), 3.08-3.21 (m, 1H), 3.25 (dd, J=7.4, 4.6 Hz, 1H), 6.41-6.48 (m, 1H), 6.52 (dd, J=10.2, 2.6 Hz, 1H), 6.58 (dd, J=8.4, 3.6 Hz, 1H).

HRMS (ESI, negative) calcd for $C_{11}H_{11}Cl_2N_2O_3S_2$ $[M-H]^-$ 352.9594; found 352.9592.

At the same time, the presence of D-luciferin 3C, which is produced by intramolecular cyclization of the substituted diaminodithioether (Novel Compound 2C), was also confirmed.

HRMS (ESI, negative) calcd for $C_{11}H_7N_2O_3S_2$ $[M-H]^-$ 278.9904; found 278.9901.

(Example 9) Production of D-Luciferin Derivative 3A

[Formula 25]

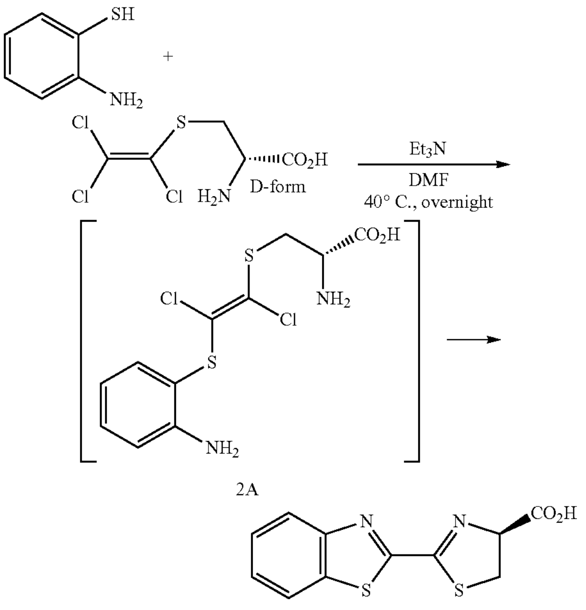

2A

3A wherein Et represents an ethyl group.

To a glass flask was added 2 mL of DMF and 246.0 mg, 0.98 mmol of S-(1,2,2-trichlorovinyl)-D-cysteine (substituted D-cysteine obtained in Example 1), and stirring was started. Then, 118.1 mg, 1.2 mmol of $Et_3N$ was added, and the mixture was heated to 40° C. 63.2 mg, 0.51 mmol of 2-aminobenzenethiol was added, and the mixture was allowed to react overnight while heated to 40° C. After heating, the mixture was brought back to room temperature, and 4 mL of distilled water was added. Then, the mixture was adjusted to pH 3 with 1M hydrochloric acid, extracted with ethyl acetate (4 mL×3), and washed with saturated brine (4 mL×1). The organic phase was dried over sodium sulfate, filtered, and the solvent was removed from the reaction solution in an evaporator to give a D-luciferin derivative (3A). In the present reaction, it is believed to be obtained via a middle step of forming a substituted diaminodithioether (Novel Compound 2A).

HRMS (ESI, negative) calcd for $C_{11}H_7N_2O_2S_2$ $[M-H]^-$ 262.9954; found 262.9949.

(Example 10) Production of D-Luciferin Derivative 3B

[Formula 26]

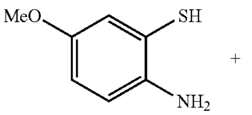

-continued

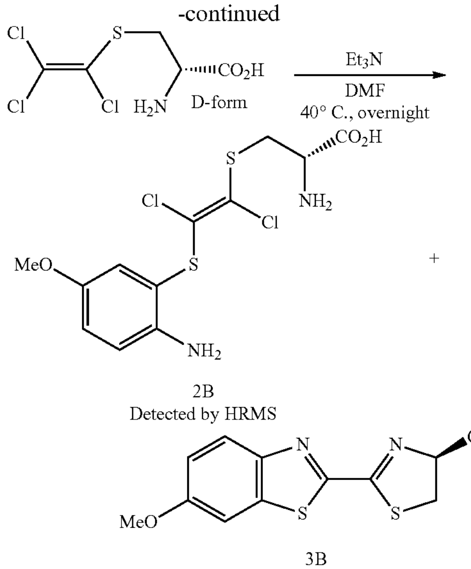

2B
Detected by HRMS

3B
Detected by HRMS wherein Me represents a methyl group and Et represents an ethyl group.

To a glass flask was added 2 mL of DMF and 249.7 mg, 1.0 mmol of S-(1,2,2-trichlorovinyl)-D-cysteine (substituted D-cysteine obtained in Example 1), and stirring was started. Then, 133.6 mg, 1.3 mmol of $Et_3N$ was added, and the mixture was heated to 40° C. 77.6 mg, 0.5 mmol of 2-amino-5-methoxybenzenethiol was added, and the mixture was allowed to react overnight while heated to 40° C.

After heating, the mixture was brought back to room temperature, and 4 mL of 1M NaOH aqueous solution was added to stop the reaction.

The mixture was extracted with ethyl acetate (4 mL×1), and washed with 1M NaOH aqueous solution (4 mL×2) and distilled water (4 ml×1). The organic phase was dried over sodium sulfate, filtered, and the solvent was removed in an evaporator.

Substituted diaminodithioether (Novel Compound 2B) and D-luciferin derivative (3B) were confirmed by HRMS. In the present reaction, it is believed to be obtained via a middle step of forming a substituted diaminodithioether (Novel Compound 2B).

Substituted Diaminodithioether (Novel Compound 2B)

HRMS (ESI, negative) calcd for $C_{12}H_{13}N_2O_3Cl_2S_2$ $[M-H]^-$ 366.9750; found 366.9739.

D-Luciferin Derivative (3B)

HRMS (ESI, negative) calcd for $C_{12}H_9N_2O_3S_2$ $[M-H]^-$ 293.0060; found 293.0053.

(Example 11) Production of D-Luciferin 3C

[Formula 27]

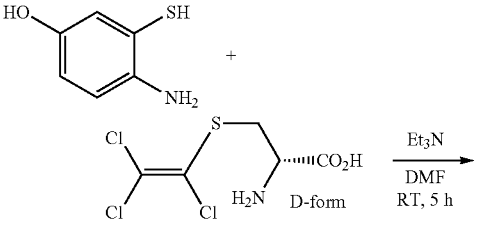

-continued

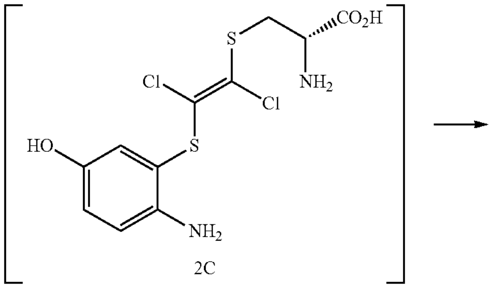

2C

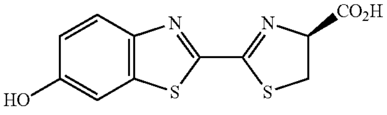

3C
Detected by HRMS

-continued

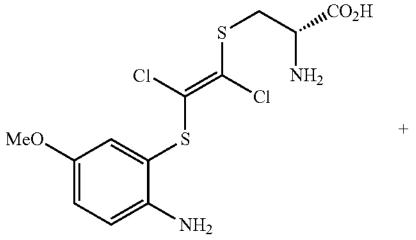

2B
Detected by HRMS

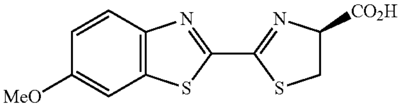

3B
Detected by HPLC
Detected by HRMS wherein Et represents an ethyl group.

A glass flask was wrapped with aluminum foil and kept in the dark. 250.7 mg, 1.0 mmol of S-(1,2,2-trichlorovinyl)-D-cysteine, 2 mL of DMF, 0.5 mL of $Et_3N$, and 75.6 mg, 0.54 mmol of 2-amino-5-hydroxybenzenethiol were added thereto and the mixture was allowed to react at room temperature for 5 hours. 4 mL of distilled water was added to stop the reaction. The reaction solution was adjusted to pH 3 with 1M HCl aqueous solution, extracted with AcOEt (20 mL×3), and dried over sodium sulfate. After filtration, the filtrate was concentrated to give D-Luciferin (3C). In (Example 8), in addition to the precursor substituted diaminodithioether 2C, D-luciferin (3C), which is obtained by the next reaction, that is, the intramolecular cyclization of substituted diaminodithioether 2C, was also obtained, and therefore in the present reaction described in (Example 11), D-luciferin (3C) is believed to be obtained via a middle step of forming a substituted diaminodithioether (Novel Compound 2C).

HRMS (ESI, negative) calcd for $C_{11}H_7N_2O_3S_2$ $[M-H]^-$ 278.9904; found 278.9902.

(Example 12) Production of D-Luciferin Derivative 3B

[Formula 28]

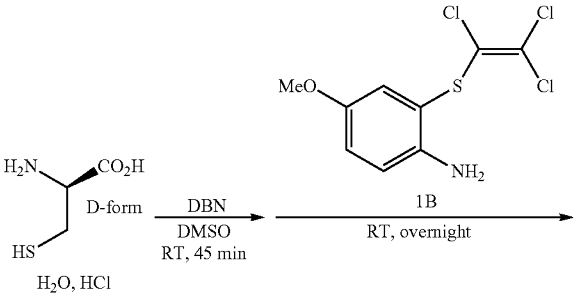

wherein Me represents a methyl group.

To a glass flask was added 70.4 mg, 0.4 mmol of D-cysteine hydrochloride monohydrate, 1 mL of DMSO, and 126.6 mg, 1.0 mmol of DBN, and the mixture was stirred at room temperature for 45 minutes. Then, 114.6 mg, 0.4 mmol of substituted 2-amino-5-methoxybenzenethiol (Novel Compound 1B) was added and the mixture was stirred overnight. 4 mL of distilled water was added and the mixture was stirred overnight, then filtered to give a solid (92.6 mg).

Reversed phase HPLC analysis of the solid with water and acetonitrile showed a peak at the same retention time as that of a sample compound 3B synthesized separately according to Non-Patent Literature 6 (J. Am. Chem. Soc., 2012, 134, 7604), which confirmed the presence of compound 3B. In addition, HRMS analysis also confirmed the presence of compound 3B and compound 2B.

D-Luciferin Derivative 3B

HRMS (ESI, negative) calcd for $C_{12}H_9N_2O_3S_2$ $[M-H]^-$ 293.0060; found 293.0062.

Substituted Diaminodithioether 2B

HRMS (ESI, negative) calcd for $C_{12}H_{13}N_2O_3Cl_2S_2$ $[M-H]^-$ 366.9750; found 366.9752.

(Example 13) Production of D-Luciferin 3C

[Formula 29]

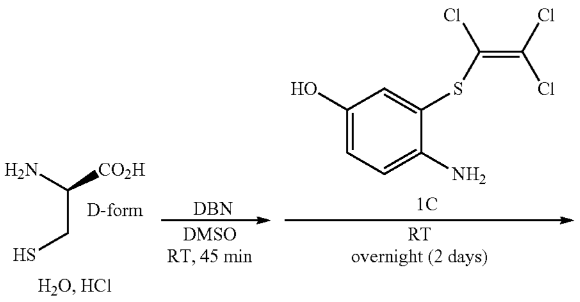

-continued

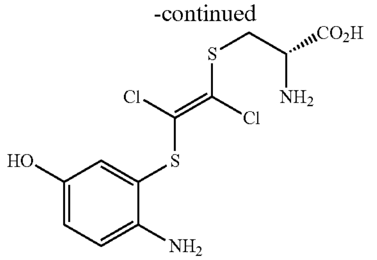

2C

+

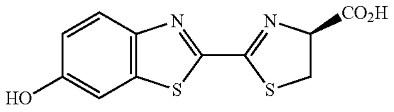

3C
Detected by HPLC
Detected by HRMS

To a glass flask was added 70.4 mg, 0.4 mmol of D-cysteine hydrochloride monohydrate, 1 mL of DMSO, and 182.4 mg, 1.5 mmol of DBN, and the mixture was stirred at room temperature for 45 minutes. Then, 108.3 mg. 0.4 mmol of substituted 2-amino-5-hydroxybenzenethiol (Novel Compound 1C) was added and the mixture was stirred for two nights. 4 mL of distilled water was added, and the mixture was stirred overnight, then adjusted to pH 11 with 1M NaOH aqueous solution, and washed with diethyl ether ($Et_2O$) (10 mL×3). Then, the aqueous layer was adjusted to pH 3 with 1M HCl aqueous solution, and extracted with ethyl acetate (AcOEt) (10 mL×5). There, the insoluble material was removed by filtration, and then the organic layer was dried over sodium sulfate. The drying agent sodium sulfate was removed by filtration, and the filtrate was concentrated in an evaporator to give a solid (20.1 mg).

Reversed phase HPLC analysis of the solid with water and acetonitrile showed a peak at the same retention time as that of a sample compound 3C synthesized separately according to Non-Patent Literature 6 (J. Am. Chem. Soc., 2012, 134, 7604), which confirmed the presence of compound 3C. In addition, HRMS analysis also confirmed the presence of compound 3C. At the same time, the presence of substituted diaminodithioether (Novel Compound 2C) was confirmed by HRMS analysis (positive).

D-Luciferin 3C

HRMS (ESI, negative) calcd for $C_{11}H_7N_2O_3S_2$ $[M-H]^-$ 278.9904; found 278.9903.

Substituted Diaminodithioether (Novel Compound 2C)

HRMS (ESI, positive) calcd for $C_{11}H_{12}Cl_2N_2O_3S_2Na$ $[M+Na]^+$ 376.9559; found 376.9579.

(Example 14) Production of Substituted 2-Amino-5-hydroxybenzenethiol 1C

[Formula 30]

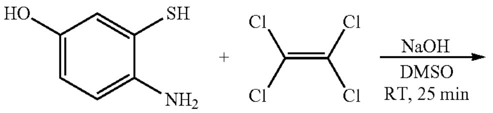

-continued

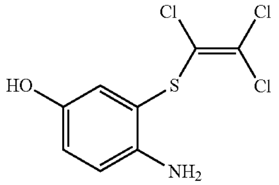

1C

To a glass flask was added 2 mL of DMSO, 829.6 mg. 5.0 mmol of tetrachloroethylene, 123.3 mg, 3.1 mmol of NaOH, and 77.5 mg, 0.55 mmol of 4-amino-3-mercaptophenol, and the mixture was allowed to react for 25 minutes. 4 mL of distilled water was added to stop the reaction, and the reaction solution was concentrated in an evaporator. The obtained concentrate was dissolved in methanol, filtered, and then concentrated in an evaporator. The obtained concentrate was dissolved in a small amount of methanol and precipitated in a mixed solution of Et2O and hexane. After filtering the precipitate, the filtrate was concentrated in an evaporator, and purified by column chromatography to give 5.9 mg of substituted 2-amino-5-hydroxybenzenethiol (Novel Compound 1C) with a 4% yield with respect to 4-amino-3-mercaptophenol.

$^1H$ NMR (300 MHZ, $CDCl_3$) δ 6.69 (d, J=8.1, 1H), 6.81 (dd, J=8.9, 2.9 Hz, 1H), 6.94 (d, J=3.0 Hz, 1H).

HRMS (ESI, negative) calcd for $C_8H_5Cl_3NOS$ $[M-H]^-$ 267.9163; found 267.9160.

The method for producing D-luciferin and a D-luciferin derivative of the present invention is based on a novel synthetic route, and therefore the reaction intermediates include novel compounds. For example, the following substituted D-cysteine is a known compound, but the intermediates 1A, 1B, 1C, 2A, 2B, and 2C, which belong to the other two general formulas, are novel compounds as far as the applicant has investigated. In the following formulas, Me represents a methyl group.

[Formula 31]

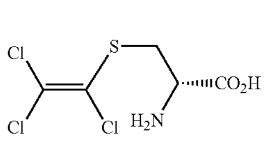

Substituted D-cysteine
Known compound

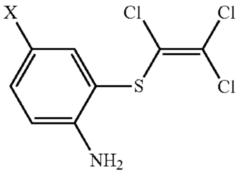

1A (X = H)
1B (X = OMe)
1C (X = OH)
Substituted 2-aminobenzenethiols (1A, 1B and 1C)
Novel compounds -continued

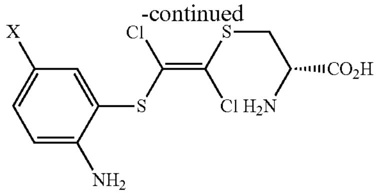

2A (X = H)
2B (X = OMe)
2C (X = OH)
Substituted diaminodithioethers (2A, 2B and 2C)
Novel compounds

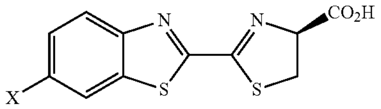

3A (X = H)
3B (X = OMe)
3C (X = OH)
D-Luciferin derivatives (3A and 3B) and D-luciferin (3C)

The invention claimed is:

1. A substituted diaminodithioether represented by the following formula (1):

(1)

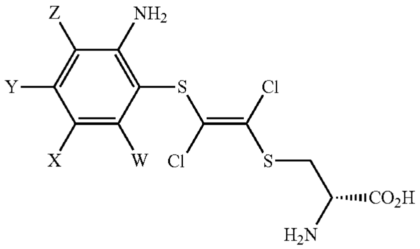

wherein X is H, $OCH_3$ or OH; and Y, Z and W are H or monovalent organic groups selected from the group consisting of alkyl groups, N, N-disubstituted amino groups, alkoxy groups, aryl groups, and aryloxy groups.

2. A method for producing a substituted diaminodithioether represented by the following formula (1):

(1)

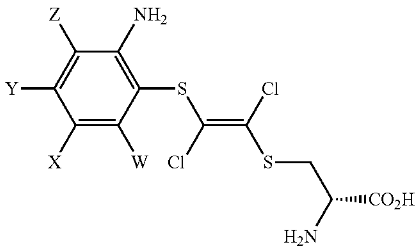

wherein X is H, $OCH_3$ or OH; and Y, Z and W are H or monovalent organic groups selected from the group consisting of alkyl groups, N, N-disubstituted amino groups, alkoxy groups, aryl groups, and aryloxy groups, the method comprising the step of:

(a) reacting a substituted D-cysteine represented by the following formula (2):

(2)

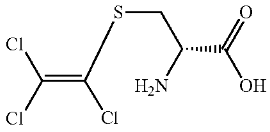

with an o-aminobenzenethiol derivative represented by the following formula (3):

(3)

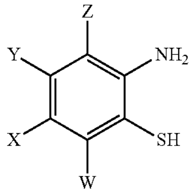

wherein X is H, $OCH_3$ or OH; and Y, Z and W are H or monovalent organic groups selected from the group consisting of alkyl groups, N, N-disubstituted amino groups, alkoxy groups, aryl groups, and aryloxy groups, in the presence of a base.

3. A method for producing D-luciferin and a D-luciferin derivative represented by the following formula (4):

(4)

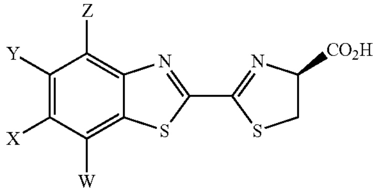

wherein X is H, $OCH_3$ or OH; and Y, Z and W are H or monovalent organic groups selected from the group consisting of alkyl groups, N, N-disubstituted amino groups, alkoxy groups, aryl groups, and aryloxy groups, the method comprising the step of:

(b) cyclizing substituted diaminodithioether represented by formula (1)

(1)

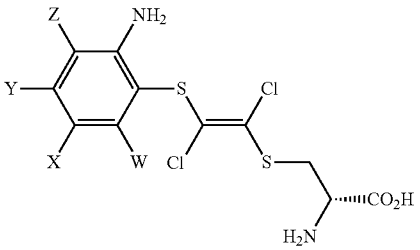

in the presence of a base.

4. The method for producing D-luciferin and a D-luciferin derivative represented by formula (4) according to claim 3, wherein the substituted diaminodithioether represented by formula (1) is obtained by the step of (a) reacting a substituted D-cysteine represented by formula (2)

(2)

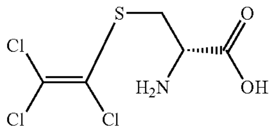

with an o-aminobenzenethiol derivative represented by formula (3)

(3)

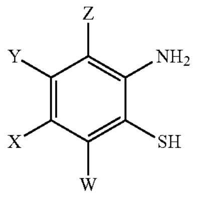

in the presence of a base.

5. The method according to claim 2, wherein the substituted D-cysteine represented by formula (2) is obtained by reacting tetrachloroethylene with D-cysteine in the presence of a base.

6. A method for producing a substituted diaminodithioether represented by the following formula (1):

(1)

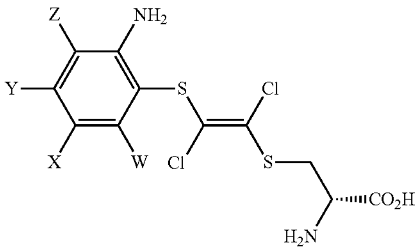

wherein X is H, $OCH_3$ or OH; and Y, Z and W are H or monovalent organic groups selected from the group consisting of alkyl groups, N, N-disubstituted amino groups, alkoxy groups, aryl groups, and aryloxy groups, the method comprising the step of:

(c) reacting an aminothioether derivative represented by the following formula (5):

(5)

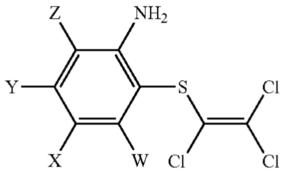

wherein X, Y, Z and W are as described above, with D-cysteine in the presence of a base.

7. The method for producing D-luciferin and a D-luciferin derivative represented by formula (4) according to claim 3, wherein the substituted diaminodithioether represented by formula (1) is obtained by the step of (c) reacting an aminothioether derivative represented by formula (5)

(5)

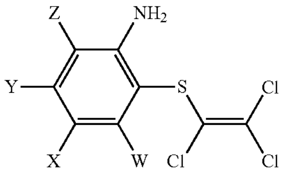

with D-cysteine in the presence of a base.

8. The method according to claim 6, wherein the aminothioether derivative represented by formula (5) is obtained by reacting an o-aminobenzenethiol derivative represented by the following formula (3):

(3)

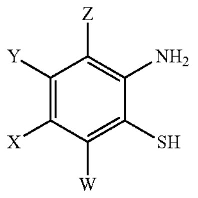

wherein X, Y, Z and W are as previously described, with tetrachloroethylene in the presence of a base.

9. The method according to claim 2, wherein the base is selected from the group consisting of NaOH, DBN, and triethylamine.

10. The method according to claim 3, wherein the base is selected from the group consisting of NaOH, DBN, and triethylamine.

11. The method according to claim 4, wherein the base is selected from the group consisting of NaOH, DBN, and triethylamine.

12. The method according to claim 5, wherein the base is selected from the group consisting of NaOH, DBN, and triethylamine.

13. The method according to claim 6, wherein the base is selected from the group consisting of NaOH, DBN, and triethylamine.

14. The method according to claim 7, wherein the base is selected from the group consisting of NaOH, DBN, and triethylamine.

15. The method according to claim 8, wherein the base is selected from the group consisting of NaOH, DBN, and triethylamine.

* * * * *